(12) United States Patent
Wu

(10) Patent No.: US 6,703,356 B1
(45) Date of Patent: Mar. 9, 2004

(54) SYNTHETIC HYDROCARBON FLUIDS

(75) Inventor: Margaret M. Wu, Skillman, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 09/533,432

(22) Filed: Mar. 23, 2000

(51) Int. Cl.[7] .................................................. C07C 2/66
(52) U.S. Cl. ........................... 508/591; 585/10; 585/12; 585/18; 585/255
(58) Field of Search ............................... 585/10, 11, 12, 585/18, 255; 508/591

(56) References Cited

U.S. PATENT DOCUMENTS

| 4,016,218 A | * | 4/1977 | Haag et al. ............... 585/18 |
| 4,282,392 A | * | 8/1981 | Cupples et al. ............ 585/10 |
| 4,547,609 A | | 10/1985 | Dessau ..................... 585/517 |
| 4,568,786 A | | 2/1986 | Hsia Chen et al .......... 585/517 |
| 4,962,249 A | * | 10/1990 | Chen et al. ................ 585/329 |
| 5,026,919 A | * | 6/1991 | Dessau ...................... 568/433 |
| 5,113,030 A | * | 5/1992 | Chen et al. .................. 585/10 |
| 5,120,891 A | | 6/1992 | Sanderson et al .......... 585/533 |
| 5,171,908 A | * | 12/1992 | Rudnick ...................... 585/12 |
| 5,180,864 A | * | 1/1993 | Sanderson et al. ............ 585/10 |
| 5,210,347 A | | 5/1993 | Chen et al .................... 585/14 |
| 5,453,556 A | | 9/1995 | Chang et al ................ 585/524 |
| 5,780,382 A | * | 7/1998 | Chang et al. ............... 508/309 |
| 6,071,864 A | * | 6/2000 | His Ho et al. .............. 508/591 |

FOREIGN PATENT DOCUMENTS

| EP | 0564728 A1 | 10/1993 | ............. C07C/2/12 |
| EP | 0673352 B1 | 4/1999 | ............. C07C/2/12 |
| WO | WO 93/16020 | 8/1993 | ............. C07C/2/12 |

* cited by examiner

Primary Examiner—Jacqueline V. Howard
(74) Attorney, Agent, or Firm—Malcolm D. Keen

(57) ABSTRACT

The present invention provides a process for polymerizing an olefin to produce poly-olefins using a crystalline catalyst. The resulting poly-olefins have low viscosity and low volatility and may be used in various functional fluids.

31 Claims, 2 Drawing Sheets

Noack Volatility vs. 100oC Viscosity for 1-Hexadecene-BasePAO vs. Commercial PAO

SYNTHETIC HYDROCARBON FLUIDS

FIELD OF THE INVENTION

This invention relates to the polymerization of olefins using large pore crystalline catalysts to produce poly-olefins characterized by low volatility and excellent viscometic properties.

BACKGROUND OF THE INVENTION

Poly-alpha-olefins are highly useful as basestocks for functional fluids such as lubricants, transmission fluids, and transformer fluids. Poly-alpha-olefins are conventionally prepared by the polymerization of alpha-olefins using a Friedel-Crafts catalyst such as $BF_3$ or $AlCl_3$. The poly-alpha-olefin typically is then hydrogenated to stabilize the polymer against oxidation and degradation.

In a typical poly-alpha-olefin production process, 1-decene is used as the starting material (see, e.g., U.S. Pat. Nos. 3,742,082 and 4,282,392). Polymers of 1-decene and mixtures of 1-decene with 1-octene and/or 1-dodecene generally result in base fluids having a high viscosity index (VI) and low pour point. 1-decene and other linear alpha-olefins are made from ethylene. The polymerization of ethylene usually produces a wide range of alpha-olefins, from 1-butene to 1-$C_{20}$ and higher alpha-olefins, with the product distribution governed by the degree of polymerization. The higher alpha-olefins, such as $C_{14}$ or higher, generally are not used as starting materials for poly-alpha-olefin production because the resulting polymers typically have undesireable properties such as high pour point and high volatility that render them unsuitable for use as high performance functional fluids (see James A. Brennan, Wide-Temperature Range Synthetic Hydrocarbon Fluids, IND. ENG. CHEM. PROD. RES. DEV., 19, 2–6 (1980)). Accordingly, current poly-alpha-olefin manufacturing processes generally use lower alpha olefins, such as $C_8$, $C_{10}$, and $C_{12}$ alpha-olefins, as starting materials without taking advantage of the remaining higher olefins produced in the production facilities. The following is a summary of some of the prior art in this field of invention:

U.S. Pat. No. 4,218,330 discloses a process for oligomerizing higher olefins such as $C_{12-18}$ with cationic catalysts, such as boron trifluoride, to form lubricant products.

U.S. Pat. No. 3,322,848 discloses a method of manufacturing lubricating oils from $C_{10}$ to $C_{18}$ alpha olefins using a catalytic agent prepared by base exchanging a crystalline alkali metal aluminosilicate having uniform pore openings of 6 to 15 Angstrom units with an ionizable metal compound, such as rare earth metals. This process generally resulted in low lube yields and significant amount of coke formation. Furthermore, the products made from 1-dodecene or 1-tetradecene had relatively high pour points.

U.S. Pat. No. 4,547,613 discloses the conversion of olefins by contact with a ZSM-5 type zeolite catalyst that has been conditioned by a previous contact with a light olefin preferably of three to six carbon atoms per molecule.

U.S. Pat. No. 4,517,399 discloses the conversion of $C_3$ to $C_{18}$ olefins over a ZSM-5 type catalyst to obtain a lube oil with an enhanced viscosity index. The active catalytic centers of the ZSM-5 type catalysts disclosed in this patent are located inside small and restricted channels having openings usually smaller than 5.6 Angstroms throughout the zeolite structures. These small pores impose little or no restriction for the smaller olefins, such as $C_2$, $C_3$, and $C_4$ olefins to diffuse to the active sites inside the zeolite channels and polymerize to give lube molecules with high efficiency. However, these zeolites with small and restricted channels are not very effective for conversion of large olefins into polymers because the large olefins diffuse very slowly along the small and restricted channels. Prior art attempts to drive the reaction by raising the reaction temperature or using prolonged reaction times lead to undesirable side reactions, such as double bond isomerization, skeletal isomerization, and cracking, that, in turn, decrease desirable product yields. Examples of such attempts and the accompanying side reactions are described in U.S. Pat. No. 5,523,511 (skeletal isomerization) and WO 92117 (isomerization of 1-olefins into internal olefins).

In accordance with the present invention, novel processes have now been discovered that can produce poly-olefins from olefins, and particularly from higher olefins such as $C_{14}$ and higher, using catalysts with widely open structures and having high activity for polymerization. In preferred embodiments, the novel processes of the invention utilize crystalline catalysts having constraint indices of less than about three. The resulting poly-olefins have excellent pour point, volatility and viscometric characteristics, especially when compared to poly-olefins produced from conventional catalysts, such as Friedel Crafts catalysts. In addition, these processes enable the use of higher olefins as starting material for poly-olefin manufacturing, thereby easing the demand for 1-decene as a feedstock.

SUMMARY OF THE INVENTION

The present invention provides processes for polymerizing an olefin, preferably an alpha-olefin, having from about 8 to about 30 carbon atoms. The processes utilize large pore crystalline catalysts having constraint indices of less than about three to produce poly-olefins that exhibit low viscosity and low volatility. In particular, the catalysts of the present invention provide for the use of higher olefins, such as $C_{14}$, $C_{16}$, $C_{18}$ or higher, in poly-olefin production processes.

The poly-olefins produced in accordance with the novel processes of the present invention have desirable viscosity, volatility, and pour point characteristics. In particular, the polymers of the present invention that are formed from higher alpha-olefins, such as $C_{14}$ to $C_{18}$, exhibit unexpected properties, especially when compared to conventional poly-alpha-olefins formed from $C_8$ to $C_{12}$ olefins.

DETAILED DESCRIPTION OF THE INVENTION

Figure 1:
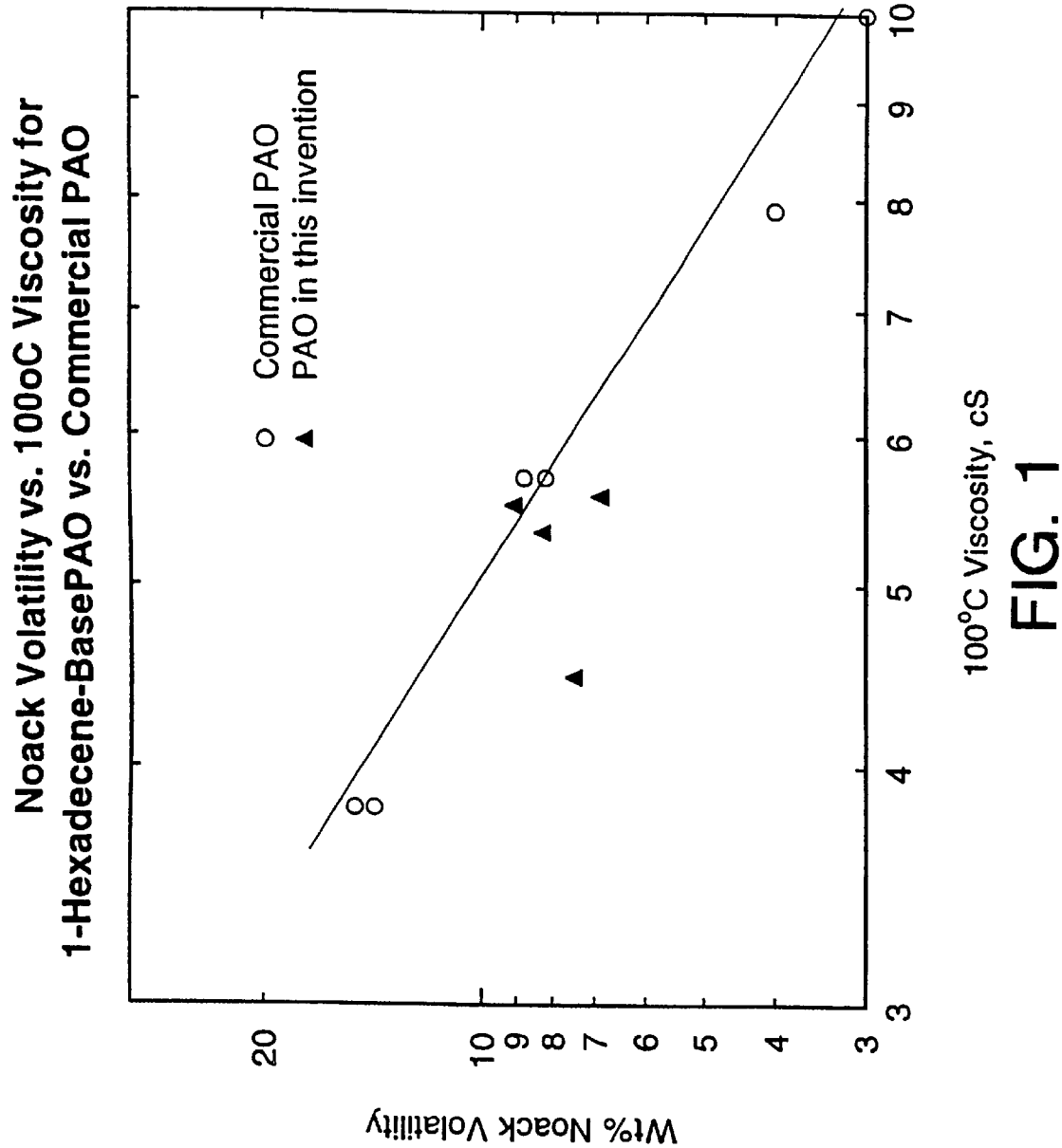
FIG. 1 is a plot of Noack volatility versus viscosity at 100° C. The Figure illustrates the volatility for poly-alpha-olefin fluids made from conventional 1-decene and a Friedel Crafts catalyst and the volatility for the poly-alpha-olefins produced pursuant to Examples 2 and 3 of the present invention.

The present invention involves processes for preparing poly-olefins from olefins using a crystalline catalyst having a constraint index of less than about three. The resulting poly-olefins have low viscosity, low volatility, and low pour points and may be used in various functional fluids.

The starting materials to be used in accordance with the present invention include olefins, defined herein as a class of unsaturated aliphatic hydrocarbons having one or more double bonds. The olefins may be alpha-olefins, internal olefins, vinylidene olefins, or mixtures thereof. Olefins with slight branching, such as those obtained from Fischer Tropsch processes, may also be used. In preferred embodiments, the present invention utilizes alpha-olefins. Although alpha-olefins are readily available in large quantities, some commercially available alpha-olefins may contain minor amounts of internal olefins and vinylidene olefins. The preferred olefins of the present invention contain over about 50 mole percent of alpha-olefins, more preferably over about 80 mole percent.

Typically, the starting olefins have from about 8 to about 30 carbon atoms, and more typically, from about 10 to about 30 carbon atoms. In more preferred embodiments, the starting olefins have from about 12 to about 24 carbon atoms, even more preferably from about 14 to about 24 carbon atoms, and even more preferably from about 16 to about 24 carbon atoms. For example, the olefins may include normal alpha or internal dodecene, tridecene, tetradecene, pentadecene, hexadecene, heptadecene, octadecene, eicosene, docosene, tetracosene, and hexacosene. Other olefins that may be used in the present invention include 2-methyl-1-undecene, 2-butyl-1-octene, 2-hexyl-1-decene, 2-octyl-1-dodecene, 2-decyl-1-tetradecene, or other similar 2-alkyl-1-alkenes.

Preferably, the starting olefins are substantially pure alpha-olefins. The poly-olefins may be made from a single olefin or from mixtures of two or more olefins. For example, 1-hexadecene by itself is a preferred starting material, as are mixtures of 1-tetradecene, 1-hexadecene, 1-octadecene, and/or $C_{20}$ to $C_{24}$ alpha-olefins in any proportion. Generally, dimers of the smallest starting olefins having more than about 26 carbon atoms are preferred polymer products and possess good volatility and viscosity characteristics.

The catalysts used to polymerize the olefins comprise large pore crystalline catalysts. Typically, the catalyst comprises an acidic, high activity zeolite. The zeolite catalysts of the present invention provide unique compositions and products with low volatility and viscosity that may be used in high performance functional fluids. In addition, mixed oxide catalysts, such as $WO_x/ZrO_2$, and acid clay catalysts may also be used.

Constraint Index (CI) is used herein in order to determine whether a catalyst provides the appropriate constrained access to the starting materials, i.e. starting olefins, used in the processes of the present invention. The method by which Constraint Index is determined is described fully in U.S. Pat. No. 4,016,218, which is incorporated herein by reference in its entirety. The catalysts which are useful in the processes of this invention are those that possess a Constraint Index of less than about three.

Constraint Index values for some typical zeolites, including some which are suitable as catalysts in the process of this invention, are set forth in Table A:

TABLE A

| | CI (at test temperatures) | |
|---|---|---|
| ZSM-4 | 0.5 | (316° C.) |
| ZSM-5 | 6–8.3 | (371° C.–316° C.) |
| ZSM-11 | 5–8.7 | (371° C.–316° C.) |
| ZSM-12 | 2.3 | (316° C.) |
| ZSM-20 | 0.5 | (371° C.) |
| ZSM-22 | 7.3 | (427° C.) |
| ZSM-23 | 9.1 | (427° C.) |

TABLE A-continued

| | CI (at test temperatures) | |
|---|---|---|
| ZSM-34 | 50 | (371° C.) |
| ZSM-35 | 4.5 | (454° C.) |
| ZSM-48 | 3.5 | (538° C.) |
| ZSM-50 | 2.1 | (427° C.) |
| MCM-22 | 1.5 | (454° C.) |
| TMA Offretite | 3.7 | (316° C.) |
| TEA Mordenite | 0.4 | (316° C.) |
| Clinoptilolite | 3.4 | (510° C.) |
| Mordentite | 0.5 | (316° C.) |
| REY | 0.4 | (316° C.) |
| Amorphous Silica-alumina | 0.6 | (538° C.) |
| Dealuminized Y | 0.5 | (510° C.) |
| Erionite | 38 | (316° C.) |
| Zeolite Beta | 0.6–2.0 | (316° C.–399° C.) |

It is to be realized that the above CI values typically characterize the specified catalysts but that such are the cumulative result of several variables useful in the determination and calculation thereof. Thus, for a given zeolite exhibiting a CI value of less than about three, depending on the temperature employed during the test method within the range of 290° C. to about 538° C., with accompanying conversion between 10% and 60%, the CI may vary within the indicated range of about three or less. Accordingly, it will be understood to those skilled in the art that the CI as utilized herein, while affording a highly useful means for characterizing the catalysts of interest, is approximate taking into consideration the manner of its determination with the possibility in some instances of compounding variable extremes. However, in all instances, at a temperature within the above-specified range of 290° C. to about 538° C., the CI will have a value for any given catalyst of interest herein of less than about three.

Examples of the zeolites that may be used in the present invention include ZSM-3, ZSM-4, ZSM-18, ZSM-20, ZSM-38, ZSM-50, mordenite, USY, and zeolite Beta. Many of the preferred zeolite catalysts with a CI of less than about three typically have channel systems or pore openings formed by 12-membered (or larger) oxygen rings. These large ring systems provide sufficient access to the larger olefins, e.g. $C_{14}$ and higher, used in the polymerization reactions of the present invention.

In addition, zeolites with pore openings formed by 10-membered oxygen rings may also be used in the present invention. Without intending to be limited to any particular theory, it is believed that such zeolites have a layered-sheet structure with many active sites on the surface of the layered-sheets that are open and easily accessible to the large olefins used in the polymerization reactions of the present invention. Examples of such zeolites include MCM-36, MCM-22, MCM-49 and MCM-56. MCM-36, which is described in U.S. Pat. Nos. 5,250,277 and 5,258,565, incorporated herein by reference, is a pillared material having zeolitic layers.

Mixed oxide catalysts may also be used in the polymerization of the olefins of the present invention and may include treated $WO_x/ZrO_2$, described in U.S. Pat. No. 5,780,382, incorporated herein by reference. Other catalysts that may be used include phosphotungstic acid hydrates available from Aldrich Chemical Co. and acidic clays available from Englehard Colo.

Preferably, in addition to a certain Constraint Index, the catalysts of the present invention also have high acidic activity and stable activity at temperatures greater than about 200° C. The acidic activity of a catalyst may be described by its alpha value. The alpha value of the catalyst is an approximate indication of the catalytic cracking activity of the catalyst compared to a standard catalyst. The alpha test is described in U.S. Pat. No. 3,354,078 and in *J. Catalysis,* 4, 527 (1965) and 6, 278 (1966), to which reference is made for a description of the test.

Preferably, catalysts with high alpha values ranging from about 0.5 to about 1000 may be used in the present invention, more preferably from about 2 to about 1000, and even more preferably from about 20 to about 500.

Examples of preferred catalysts for use in the present invention include MCM-22, MCM-36, MCM-56, MCM-49, USY, beta, and ZSM-4.

MCM-22 is described in U.S. Pat. No. 4,954,325, incorporated herein by reference.

MCM-49 is described in U.S. Pat. No. 5,236,575, incorporated herein by reference.

MCM-56 is described in U.S. Pat. No. 5,362,697, incorporated herein by reference. Further description of MCM-22, MCM-49, and MCM-56 may be found in U.S. Pat. No. 5,600,048, incorporated herein by reference.

Zeolite USY is a material of commerce, available in large quantities as a catalyst for the cracking of petroleum. It is produced by the stabilization of zeolite Y by a procedure of repeated ammonium exchange and controlled steaming. Processes for the production of zeolite USY are described in U.S. Pat. Nos. 3,402,966 (McDaniel), 3,923,192 (Maher) and 3,449,070 (McDaniel); see also Wojciechowski, Catalytic Cracking, Catalysts, Chemistry and Kinetics, Chemical Industries, vol. 25, Marcel Dekker, New York, 1986, ISBN 0-8247-7503-8, to which reference is made for a description of zeolite USY, its preparation and properties.

Zeolite beta is described in U.S. Pat. No. 3,308,069, incorporated herein by reference.

ZSM-4 is described in U.S. Pat. No. 3,923,639, incorporated herein by reference.

Additionally, other catalysts that may be used in the present invention include a zeolite having both ammonium and protonic species associated with the exchangeable sites of the zeolite. Such catalysts are disclosed in U.S. Pat. No. 5,457,254, Artdito et al., incorporated herein by reference.

Preferably, the catalysts of the present invention comprise the hydrogen form of the zeolite. The aluminosilicate framework of the zeolite catalysts typically have many negatively charged tetrahedral aluminum sites. These negative charges associated with the zeolite framework are balanced with exchangeable cations that typically comprise alkali metals, such as sodium or potassium ions. The zeolites may be converted into hydrogen form zeolites when the cationic sodium or potassium is exchanged with a positively charged proton. Such a hydrogen form of the zeolite is preferred in promoting the olefin polymerization reaction disclosed in the present invention. In addition, the hydrogen form of mixed oxide, phosphotungstic acid hydrates, and acidic clay catalysts are also preferred.

Other catalyst properties affecting the production of poly-olefins may include: the silica-to-alumina ratio, metal modification, crystal size, and catalyst binder. For most zeolites like MCM-22, MCM-56, and MCM-36, the zeolites with lower silica-to-alumina ratio generally have higher alpha-values, and therefore, higher activity. Typically, a silica-to-alumina ratio from about 5 to about 1000 may be used, more preferably from about 10 to about 300. For other zeolites, such as zeolite Y, USY, or de-aluminized Y, a higher silica-to-alumina ratio, i.e. greater than five, may provide for higher activity, which is desirable because the zeolites age slower.

The zeolites of the present invention may also be modified with other metal components to improve such properties as activity, aging, regeneration, and stability. Examples of modifying metal components include Group IIIB, IVB, VB, VIB, VIIB, VII, and rare earth metal cations. The amount of the metal usually should not be so high as to inhibit the diffusion of reactants and products to and from the active centers of the catalyst. Typically, the amount of modifying metal is less than 10 wt %, based on the total weight of the catalyst, and may be prepared by typical impregnation methods.

The crystal size of the zeolites of the present invention may also affect poly-olefin production. Generally, zeolites having smaller crystal size will be preferred because they provide more surface area to allow reactant and product to diffuse to and from the active center of the zeolite. However, the crystal size should not be too small so as to lose catalytic stability. Typically, the zeolites of the present invention have crystal sizes from about 0.01 to about 5 microns, more preferably from about 0.01 to about 2.

The catalyst of the present invention may be composited with a matrix material or binder which is resistant to the temperatures and other conditions employed in the present process. The binder materials may include inactive materials, such as synthetic or naturally occurring zeolites as well as inorganic materials such as clays, silica, alumina, or silica-alumina. The latter may be either naturally occurring or in the form of gelatinous precipitates or gel including mixtures of silica and metal oxides. Binders which may be incorporated to improve the crush strength and other physical properties of the catalyst under commercial processing conditions include, but are not limited to, naturally occurring clays, e.g., bentonite and kaolin, as well as silica, alumina, zirconia, titania, and mixtures thereof.

The polymerization reaction is conducted such that the olefins and the catalyst are contacted in a suitable reaction zone such as, for example, in a continuous fixed bed flow reactor containing a fixed bed of the catalyst composition, under effective reaction conditions. Other reactors include a batch reactor where the catalyst and starting olefins are mixed together with stirring in a reactor over a certain amount of time and at a certain temperature, or a continuous stir tank reactor (CSTR) where the catalyst and starting olefins are continuously added to a stirring reactor and the product and catalyst are continuously removed form the stir tank, or a spinning-basket type reactor where the catalyst is suspended in a basket and olefins are continuously charged to the reactor and products are continuously withdrawn from the reactor.

Polymerization reaction conditions typically include a temperature of from about 100° C. to about 300° C., preferably from about 150° C. to about 250° C.

Typical reaction pressures include a pressure from about 0.1 to about 100 atmospheres, preferably from about 0.5 to about 50 atmospheres. The required pressure maybe maintained by inert gas pressurization, preferably with nitrogen and/or hydrogen.

Typical reaction times are from about 0.5 to about 100 hours, preferably from about 1 to about 5 0 hours in a batch reactor. The reaction time is dependent on temperature and the amount of catalyst used in the process. Generally, higher reaction temperatures and a higher catalyst charge promote faster reaction rates.

Generally, the amount of catalyst charged is about 0.1 wt % to about 15 wt % of the reaction mixture in a slurry batch reactor. A lower catalyst charge may cause longer reaction times and a higher catalyst charge may be uneconomical to run, causing filter plugging during the catalyst removal step. Preferably, the catalyst charge is about 0.2 wt % to about 10 wt %. The reaction may be carried out in a fixed-bed continuous operation where the catalyst is in pellet or extruded form and packed in a tubular reactor heated to a desirable temperature. In a fixed bed type operation, the feed may be introduced at from about 0.1 g/g of catalyst/hr to about 20 g/g of catalyst/hour. Preferred rates are from 0.2 g/g of catalyst/hr to about 10 g/g of catalyst/hr.

The polymer mixture after the reaction may contain unreacted monomer, dimer, trimer, or tetramer. Generally, fluids high in dimer and trimer are preferable products because they typically have low viscosities and may be used in formulations for wide-cross grade engine lubricants. Fluids high in tetramer or pentamer polymers typically have higher viscosity and may be used in industrial oils as well as engine oils. Generally, higher reaction temperatures, longer reaction times, and higher amounts of catalyst charge tend to increase the amounts of polymers with a higher amount of monomers.

Typically, the unreacted monomers are removed from the mixture by distillation and may be recycled or reused in subsequent poly-olefin synthesis. After stripping monomer, the reaction mixture is comprised of dimers, trimers, tetramers and other higher polymers of the starting olefin or olefin mixture. Depending on the desired application of the poly-olefins, certain polymers may be preferred and may be isolated through distillation. For example, as noted above, dimers of the starting olefin or olefin mixture are typically preferred for use in engine oil formulations because dimers generally provide the best combination of low viscosity and low volatility. Examples of preferred products include dimers from $C_{14}$, $C_{16}$, $C_{18}$, and $C_{20}$ olefins. The co-dimers of $C_{14}$ and $C_{16}$ olefins, e.g. $C_{14}/C_{18}$, $C_{14}/C_{20}$, $C_{16}/C_{18}$, or $C_{14}/C_{16}/C_{18}$ are particularly useful as lube basestocks. Generally, the content of dimer or co-dimer may be greater than 30 wt %, more preferably greater than 60 wt %, of the reaction product.

In a preferred embodiment, the polymerization product comprises dimers of alpha olefins, either pure or mixtures, with more than fourteen carbon atoms, including 1-tetradecene, 1-hexadecene, and 1-octadecene. Typically, the poly-alpha-olefins comprise greater than about 40 wt % dimer and more preferably greater than about 60 wt % dimer of these alpha-olefins.

The lube products of the present invention may comprise higher oligomers such as trimer and tetramer. Typically, the polymerization product may comprise about 1 to about 80 wt % trimer of the starting olefins, more preferably about 2 to about 40 wt %, and even more preferably about 2 to about 30 wt %. A typical olefin oligomer mixture may comprise about 50 to about 98 wt % dimer and about 2 to about 40 wt % trimer, with the remaining product comprised of tetramer or other higher oligomers. In a preferred oligomer mixture, the composition comprises about 60 to about 98 wt % dimer and about 2 to about 40 wt % trimer.

The resultant product is next typically hydrogenated by conventional methods. For example, a palladium on carbon catalyst, or nickel on Kieselguhr catalyst, or other well known hydrofinishing catalyst may be used. Hydrogenation conditions include temperatures of from about 25° C. to about 400° C. and hydrogen pressure of about 1 to about 100 atmospheres. The hydrogenated product generally has a low bromine number of less than about 2 as measured by ASTM method 1159. The hydrogenated residual may be distilled to isolate a lube product comprising the desired polymer or polymers.

In a preferred embodiment, the chemical structure of the hydrogenated dimer is:

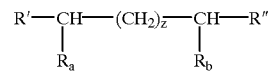

wherein each of R', R", $Ra_a$, and $R_b$ is an alkyl group having from about 1 to about 28 carbon atoms, preferably from 1 to about 16 carbon atoms, and more preferably from about 1 to about 12 carbon atoms; and z is an integer from about 1 to about 10. Preferably, the sum of the number of carbons in R' and $R_a$ is less than the smallest number of carbons in the starting olefin or olefins. Likewise, the sum of the number of carbons in R" and $R_b$ is less than the smallest number of carbons in the starting olefin or olefins. One skilled in the art will recognize that the total number of carbons in the dimer or co-dimer will be twice the number of carbon atoms in the starting monomer or monomers. For example, if the starting olefin is 1-hexadecene, the sum of the number of carbon atoms in R' and $R_a$ would be less than 16 as would the sum of the number of carbon atoms in R" and $R_b$, with the total number of carbons in the dimer being thirty-two.

The chemical structure of the poly-olefins produced in accordance with the present invention (see, e.g., Table 3) contribute to many of its improved properties. For example, hydrogenated poly-olefins of the present invention are characterized by pour points below about −10° C., preferably below −15° C., more preferably below −20° C. (Herzog pour point apparatus). Typically the pour points range from about −15 to about −85° C. These poly-alpha-olefins also maintain an excellent viscosity index of greater than about 90, more preferably greater than about 100 (ASTM D445). Typically, the viscosity index ranges from about 100 to about 170. The poly-alpha-olefins generally have viscosities at 100° C. of above about 3 cS, more preferably above about 3 cS (ASTM D445). Typically, the poly-alpha-olefins of the present invention generally have viscosities at 100° C. ranging from about 2.5 cS to about 10 cS, more preferably from about 3.3 cS to about 8.0 cS.

As demonstrated in the examples, the hydrogenated poly-olefins also maintain a low volatility. For example, the polymer and polymer mixtures of the present invention typically have a Noack volatility of below about 35 wt %, more preferably below about 25 wt %. Typically, the poly-alpha-olefins have a Noack volatility ranging from about 2 to about 35 wt %, more preferably from about 2 to about 25 wt %. For a detailed description of Noack volatility measurements see K. Noack, Agnew Chem., 49,385 (1936) or test method DIN 58–581. FIG. 1 plots product volatility versus viscosity. The solid line represents the volatility of a set of commercial poly-alpha-olefin fluids, available from a commercial source such as Mobil Chemical Co. or Chevron Chemical Co., made from 1-decene and a Friedel Crafts catalyst. The solid squares represent the volatility of the poly-alpha-olefins produced pursuant to Examples 2 and 3 of the present invention. As FIG. 1 demonstrates, the poly-alpha-olefins of the present invention exhibit lower or equal volatilities compared to the commercially available poly-alpha-olefins.

The resultant hydrogenated poly-olefins may be used in high performance functional fluids such as automotive crankcase lubricants, various engine lubricants, and as industrial lubricants. The hydrogenated poly-olefins may be used as the sole basestock or blended with other synthetic fluids, such as alkyl aromatic fluids, esters, polyalkylene glycols, or other types of poly-alpha-olefins such as high viscosity poly-alpha-olefins or polyisobutylene (PIB), and other synthetic hydrocarbon fluids. The poly-olefins of the present invention may also be blended with mineral oil basestocks produced from conventional lubricant processing, i.e. Group I basestocks, or can be blended with specially processed basestocks such as Group II or Group III hydroprocessed basestocks, or with hydroisomerized Fischer-Tropsch fluids. Such blends may provide enhanced performance properties.

In the finished lubricants, other typical additives, such as viscosity index improver, detergent, dispersants, rust inhibitor, antiwear additives, antioxidants, extreme pressure additives, friction modifiers, pour point or cloud point depressants, demulsifiers, corrosion inhibitors, and foam inhibitors may be added to further enhance the performance properties of the product. Examples of finished lubricant products include automotive crankcase oil, engine oil, transmission fluids, automotive gear lubricants, industrial gear lubricants, grease products, compressor or pump oils, refrigeration lubricants, hydraulic fluids, metal working fluids, drilling fluids, and two-cycle engine oils.

By careful selection of the starting material, reaction conditions, and catalysts, the properties of the resulting poly-olefins may be controlled. For example, optimizing performance properties may include adjusting the size of the starting olefins such that the smallest dimers have more than about 28 carbon atoms in the final product, or choosing catalysts such as MCM-22 or MCM-56 to maximize the dimer content or by choosing the lowest possible reaction temperatures with the highest possible conversion of starting olefins to polymers. The poly-alpha-olefin basestocks for high performance automotive crankcase engine oils generally have low viscosities (<5cS at 100° C.), low pour point (<−40° C.), and low volatility (<15wt % by Noack test). The poly-alpha-olefins of the present invention may be used to formulate full synthetic or semi-synthetic (when blended with mineral or hydroprocessed basestocks) wide cross grade, fuel-efficient lubricants such as SAE 0W-20, 0W-30, 0W-40, 5W-20, 5W-30, 5W-40, 5W-50, and 5W-60 viscosity grade lubricants.

The following examples illustrate the manner of making the present compositions and the physical properties of typical products. Also, the examples demonstrate the advantages of using zeolite catalysts to produce synthetic basestock with a high VI, low pour point, and low volatility from an alpha-olefin not typically used in conventional poly-alpha-olefin synthesis.

EXAMPLES

Example 1

250 g of 1-Hexadecene and 5 grams of a $BF_3/H_3PO_4$ complex were stirred in a 500 cc round bottom flask at 40° C. under a nitrogen atmosphere for 20 hours. The reaction was terminated by quenching with a 5% NaOH solution. The organic layer was dried and distilled to remove unreacted starting material. The residual product was then hydrogenated at 60° C. and 500 psi hydrogen using 1 wt % of a 5% palladium on carbon catalyst. From this hydrogenated residual, a narrow-cut lube fraction was further distilled to isolate the mostly hydrogenated hexadecene dimer fraction. The properties are summarized in Table 1.

Example 2

250 g of 1-Hexadecene and 5 grams of a MCM-22 catalyst (alumina-bound, calcined at 500° C. and crushed to a powder) were mixed in a 500 cc round bottom flask. The mixture was heated to 200 ° C. for 20 hours under a nitrogen atmosphere. The mixture was then cooled to room temperature and filtered to remove the catalyst and a liquid product was isolated by vacuum distillation. The liquid product was then hydrogenated as in Example 1 and the lube properties summarized in Table 1. The 5.51 cS lube product had a VI of 131, a pour point of −30° C., and a 7.5% Noack volatility. Compared to the product of Example 1, the product of Example 2 had a much better pour point (−30° C. vs. −9° C.) and yet maintained an excellent VI and Noack volatility.

Example 3

A portion of the hydrogenated lube product of Example 2 was further distilled to isolate a narrow cut lube fraction containing mostly hydrogenated hexadecene dimer. The lube properties were summarized in Table 1. Again, this 4.47 cS lube basestock has a much better pour point, −35° C., than the product of Example 1 while still maintaining an excellent VI and Noack volatility.

Example 4

The procedure in Example 2 was followed except that a MCM-56 pure powder catalyst was used. A 5.1 cS fluid with a 136 VI and −31 ° C. pour point was produced.

TABLE 1

PRODUCT PROPERTIES OF EXAMPLES 1–4

| EXAMPLE | 1 | 2 | 3 | 4 |
|---|---|---|---|---|
| Reaction Temp. ° C. | 40 | 200–225 | distilled product of Example 2 | 175 |
| Catalyst | $BF_3/H_3PO_4$ | MCM-22/$Al_2O_3$ |  | MCM-56 pure powder |
| Wt % Catalyst | 4 | 2 |  | 1 |
| Reaction Time (hrs) | 20 | 20 |  | 4 |
| Lube Product Composition (wt %) |  |  |  |  |
| dimer | 99.0 | 76.0 | 99.0 | 62.4 |
| trimer | 1.0 | 24.0 | 1.0 | 26.9 |
| Others | 0 | 0 | 0 | 10.8 |
| Lube Properties |  |  |  |  |
| Viscosity @ 100° C., cS | 4.48 | 5.51 | 4.47 | 5.14 |
| Viscosity @ 40° C., cS | 18.67 | 28.8 | 21.32 | 25.40 |
| VI | 161 | 131 | 123 | 136 |
| Pour Point, ° C. | −9 | −30 | −35 | −31 |
| Noack Volatility, wt % | 6.6 | 9.1 | 7.5 | Not done |

Examples 5–13

The general procedure of Example 2 was followed using different catalysts. The results are summarized in Table 2.

TABLE 2

Effect of Different Catalysts on PAO Formation from 1-Hexadecene

| EXAMPLE NO. | 5 | 6 | 7 | 8 | 9 | 10 | 11 | 12 | 13 |
|---|---|---|---|---|---|---|---|---|---|
| Catalyst type | USY(1) | Beta | ZSM-12 | MCM-22/SiO$_2$ | MCM-22/SiO$_2$ | V-MCM56 (vanadium modified) pure crystal | H-MCM-56 | WOx/ZrO$_2$ | Fitrol 22 Acid clay |
| Catalyst Wt % | 5 | 2 | 2 | 2 | 2 | 1 | 1 | 2 | 4 |
| Temp., °C. | 250 | 200 | 200 | 200 | 250 | 200 | 200 | 200 | 200 |
| Time, Hrs. | 23 | 20 | 21 | 8 | 4 | 9 | 9 | 9 | 21 |
| C$_{16}$ Wt % Conv. | 47.1 | 40.8 | 40.4 | 84.3 | 83.1 | 84.2 | 87.2 | 52.8 | 65.9 |
| Product Selectivity, wt % | | | | | | | | | |
| light end (<C$_{16}$) | 1.7 | 3.1 | 2.4 | 2.2 | 5.3 | 2.1 | 4.1 | 0.2 | 10.8 |
| C$_{16}$—C$_{32}$ | 0.5 | 0.0 | 0.1 | 0.1 | 0.0 | 3.0 | 3.5 | 2.0 | 0.5 |
| dimer | 90.3 | 89.4 | 86.7 | 76.3 | 75.4 | 70.8 | 70.2 | 88.8 | 60.4 |
| trimer | 7.4 | 7.5 | 10.0 | 19.1 | 17.3 | 19.9 | 17.9 | 8.4 | 22.7 |
| higher | 0.0 | 0.0 | 0.9 | 2.3 | 1.9 | 4.3 | 4.3 | 0.5 | 5.5 |
| Lube Properties after hydrogenation | | | | | | | | | |
| Viscosity @100° C., cS | 5.02 | 4.92 | 5.07 | 5.33 | 5.83 | 5.57 | 5.28 | 4.69 | 6.90 |
| Viscosity@40° C., cS | 24.92 | 23.96 | 23.85 | 27.42 | 32.83 | 29.54 | 27.37 | 21.29 | 39.33 |
| VI | 131 | 133 | 147 | 130 | 121 | 129 | 128 | 143 | 135.5 |
| Pour Point, °C. | <−54 | −35 | −29 | −37 | −38 | −36 | −39 | −21 | −20 |
| Noack Volatility, wt % | | | | 8.31 | | 6.92 | | | |

Through $^{13}$C-NMR analysis the chemical structure of a poly-olefin produced using a conventional BF$_3$ catalyst (see Example 1) was compared to the chemical structure of the poly-olefin produced in accordance with the present invention (see Examples 2, 5–7, and 11–13). 90.5 MHz $^{13}$C solution NMR spectra were obtained for each example on a Bruker 360 MHz AMX spectrometer using a 10 wt % solution of the sample in CDCl$_3$, with tetramethylsilane (TMS) being the chemical shift reference. A particular structural feature in the poly-olefin that was analyzed was the number of -(CH$_2$)$_n$- units present, wherein n is greater than or equal to four. As shown in the following Table 3, the hydrocarbon fluid of the present invention contains less than about 35 wt % of -(CH$_2$)$_{n \geq 4}$- units, and more preferably less than about 30 wt % of -(CH$_2$)$_{n \geq 4}$- units.

TABLE 3

| Example | 1 | 2 | 5 | 6 | 7 | 11 | 12 | 13 |
|---|---|---|---|---|---|---|---|---|
| Catalyst | BF$_3$ | MCM-22/Al$_2$O$_3$ | USY | Beta | ZSM-12 | MCM-56 | WOx/ZrO$_2$ | Filtrol 22 Clay |
| % —CH$_2$)$_{n \geq 4}$- units | 41.5 | 20.3 | 24.5 | 22.4 | 24.1 | 19.1 | 27.7 | 22.8 |

Examples 14–17

The general procedure of Example 2 was followed using different alpha-olefins and mixed alpha-olefins as starting material. The results are summarized in Table 4.

TABLE 4

| EXAMPLE | 14 | 15 | 16 | 17 |
|---|---|---|---|---|
| Starting olefins | C$_{14}$ | C$_{18}$ | C$_{14}$/C$_{18}$ | C$_{14}$/C$_{16}$C$_{18}$ |
| Starting olefin, wt % | 100 | 100 | 50/50 | 33/33/33 |
| Catalyst | MCM-22 | MCM-22 | MCM-56 | MCM-56 |
| C$_{14}$—C$_{18}$ conversion (wt %) | 85 | 80 | 80.2 | 63.6 |

TABLE 4-continued

| EXAMPLE | 14 | 15 | 16 | 17 |
|---|---|---|---|---|
| Product Selectivity (wt %) | | | | |
| dimer | 85 | 67.9 | 93.4 | 77.1 |
| trimer | 12 | 20.6 | 6.6 | 19.6 |
| Others | 3 | 11.5 | | 3.3 |
| Lube Properties after hydrogenation | | | | |
| Viscosity @ 100° C., cS | 3.84 | 6.91 | 5.69 | 5.31 |
| Viscosity @ 40° C., cS | 17.51 | 38.83 | 30.33 | 27.29 |
| VI | 111 | 139 | 131 | 130 |
| Pour Point, °C. | −51 | −21 | −26 | −28 |

Example 18

Figure 2:
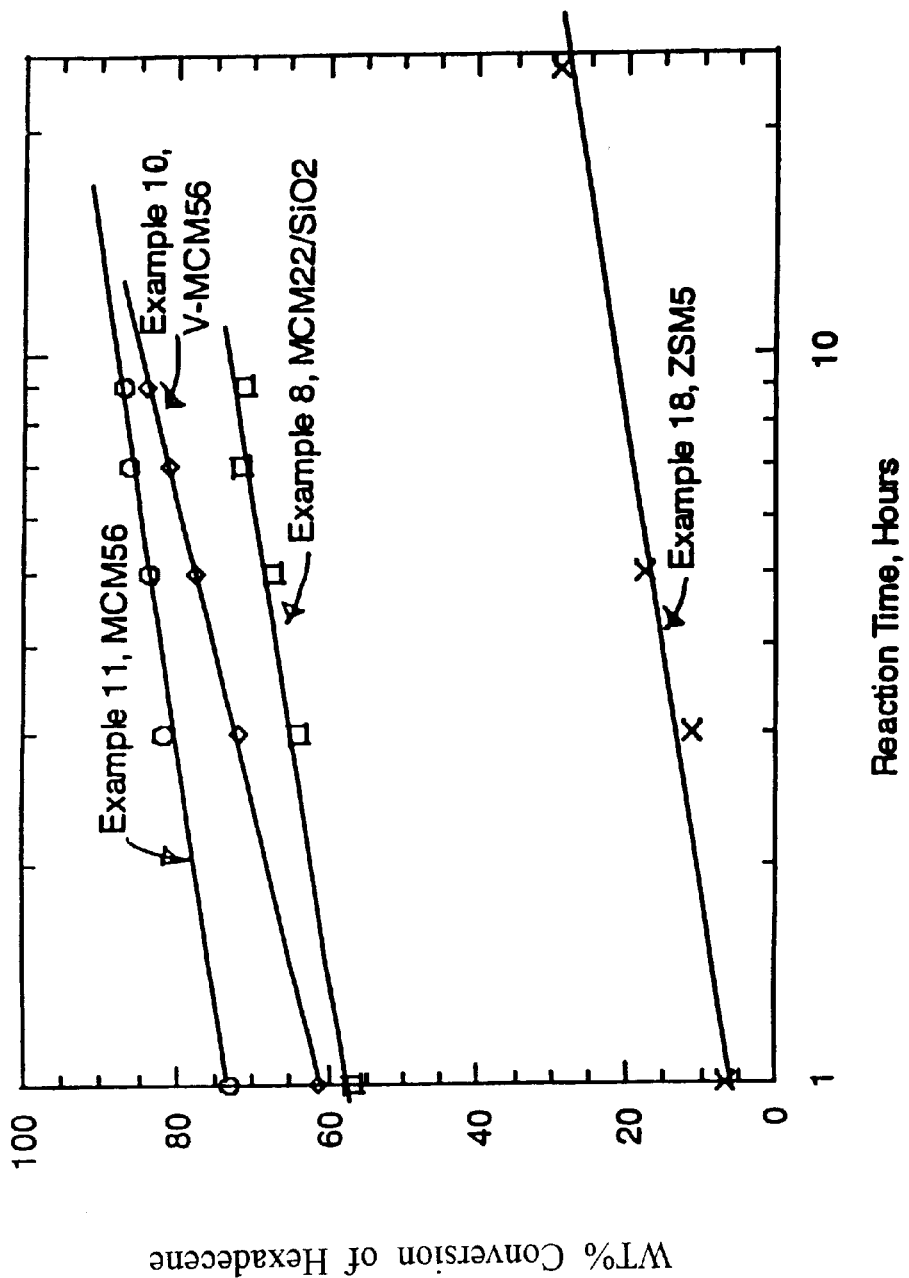
FIG. 2 illustrates the conversion (in weight percent) of 1-hexadecene using several different catalysts.

The general procedures and conditions of Examples 10 and 11 were followed, except that a ZSM-5 type catalyst was used instead of V-MCM-56 or H-MCM-56. Use of the ZSM-5 zeolite resulted in only 28% of the hexadecene being converted into lube range product after 24 hours of reaction. In the other Examples in Table 2, usually more than 40% of the hexadecene feed was converted into lube by USY, Beta or ZSM-12, and more than 80% of the feed was converted into lube by MCM-22 or MCM-56 type catalysts. The comparison is further illustrated in FIG. 2 which demonstrates that smaller pore, more highly constrained zeolites, such as ZSM-5 type catalysts, are less suitable for large olefin conversion into lube product.

Although the invention has been described in detail and with reference to specific embodiments thereof, it will be apparent to one skilled in the art that various changes and modifications can be made therein without departing from the scope and spirit of the present invention.

What is claimed is:

1. A process for polymerizing an olefin having from about 10 to about 30 carbon atoms, or mixtures thereof, comprising contacting said olefin with a crystalline catalyst having a constraint index of less than about three.

2. The process of claim 1 further comprising hydrogenating the polymerized olefin.

3. The process of claim 1 wherein the olefin comprises an alpha-olefin.

4. The process of claim 1 wherein the olefin has from about 12 to about 24 carbon atoms.

5. The process of claim 1 wherein the olefin has from about 14 to about 24 carbon atoms.

6. The process of claim 1 wherein the olefin is 1-tetradecene, 1-hexadecene, 1-octadecene, or mixtures thereof.

7. The process of claim 1 wherein the alpha-olefin is 1-hexadecene.

8. The process of claim 1 wherein the catalyst is a hydrogen form of a zeolite catalyst.

9. The process of claim 1 wherein the catalyst is at least one selected from the group consisting of zeolite MCM-22, MCM-36, MCM-49, MCM-56, USY, beta, and ZSM-4.

10. The process of claim 9 wherein the catalyst is at least one selected from the group consisting of MCM-22, MCM-36, MCM-49, and MCM-56.

11. The process of claim 1 wherein the catalyst is a mixed oxide catalyst.

12. The process of claim 1 wherein the catalyst is an acid clay catalyst.

13. A polymerized olefin prepared according to the process of claim 1.

14. A hydrogenated poly-olefin comprising an olefin having from about 10 to about 30 carbon atoms and having a viscosity above about 3 cS at 100° C., a pour point below about −15° C., and a Noack volatility of less than about 35 wt %, said poly-olefin prepared by contacting an olefin having from about 10 to about 30 carbon atoms, or mixtures thereof, with a crystalline catalyst having a constraint index of less than about three, and hydrogenating.

15. The poly-olefin of claim 14 wherein the olefin comprises an alpha-olefin.

16. The poly-olefin of claim 14 wherein the olefin has from about 12 to about 24 carbon atoms.

17. The poly-olefin of claim 14 wherein the olefin has from about 14 to about 24 carbon atoms.

18. The poly-olefin of claim 14 wherein the olefin is 1-tetradecene, 1-hexadecene, 1-octadecene, 1-eicosene, or mixtures thereof.

19. The poly-olefin of claim 14 wherein the olefin is 1-hexadecene.

20. The poly-olefin of claim 14 wherein the catalyst is at least one selected from the group consisting of zeolite MCM-22, MCM-36, MCM-49, MCM-56, USY, beta, and ZSM-4.

21. The poly-olefin of claim 20 wherein the catalyst is at least one selected from the group consisting of MCM-22, MCM-36, MCM-49 and MCM-56.

22. The poly-olefin of claim 14 wherein said poly-olefin comprises more than about 30 wt % dimer or co-dimer of said olefin.

23. The poly-olefin of claim 14 wherein said poly-olefin has less than about 35 wt % of $-(CH_2)_n-$ units wherein n is greater than or equal to four.

24. The poly-olefin of claim 14 wherein said poly-olefin comprises about 2 to about 30 wt % trimer of said olefin.

25. A lubricant oil comprising the poly-olefin of claim 14.

26. A hydrogenated poly-alpha-olefin comprising an alpha-olefin having from about 14 to about 24 carbon atoms, or mixtures thereof, and having a viscosity of at least about 3 cS at 100° C., a pour point below about −15° C., and a Noack volatility of less than about 35 wt %.

27. The poly-alpha-olefin of claim 26 wherein said poly-alpha-olefin comprises an alpha-olefin having from about 16 to about 24 carbon atoms.

28. The poly-alpha-olefin of claim 26 comprising more than about 30 wt % dimer or co-dimer of said alpha-olefin.

29. The poly-alpha-olefin of claim 26 wherein said alpha-olefin is 1-hexadecene.

30. The poly-alpha-olefin of claim 26 comprising about 2 to about 30 wt % trimer of said alpha-olefin.

31. A lubricant oil comprising the poly-alpha-olefin of claim 26.

* * * * *